US009486531B2

(12) United States Patent
Dadey et al.

(10) Patent No.: US 9,486,531 B2
(45) Date of Patent: Nov. 8, 2016

(54) DEHYDRATED HYDROGEL INCLUSION COMPLEX OF A BIOACTIVE AGENT WITH FLOWABLE DRUG DELIVERY SYSTEM

(75) Inventors: Eric Dadey, Furlong, PA (US); Andrew (Drew) Watkins, Fort Collins, CO (US)

(73) Assignee: INDIVIOR UK LIMITED, Slough (GB)

( * ) Notice: Subject to any disclaimer, the term of this patent is extended or adjusted under 35 U.S.C. 154(b) by 382 days.

(21) Appl. No.: 12/995,956

(22) PCT Filed: Jun. 3, 2009

(86) PCT No.: PCT/US2009/003361
§ 371 (c)(1),
(2), (4) Date: Feb. 22, 2011

(87) PCT Pub. No.: WO2009/148579
PCT Pub. Date: Dec. 10, 2009

(65) Prior Publication Data
US 2011/0171305 A1 Jul. 14, 2011

Related U.S. Application Data

(60) Provisional application No. 61/058,484, filed on Jun. 3, 2008.

(51) Int. Cl.
*A61K 9/00* (2006.01)
*A61K 9/06* (2006.01)
*A61K 47/34* (2006.01)
*A61K 47/32* (2006.01)
*A61K 9/19* (2006.01)

(52) U.S. Cl.
CPC ............. *A61K 47/34* (2013.01); *A61K 9/0024* (2013.01); *A61K 9/06* (2013.01); *A61K 47/32* (2013.01); *A61K 9/19* (2013.01)

(58) Field of Classification Search
CPC .... A61K 47/32; A61K 47/34; A61K 9/0024; A61K 9/06; A61K 9/19
USPC ....... 424/141.1, 484; 514/1.1, 44 R; 977/773
See application file for complete search history.

(56) References Cited

U.S. PATENT DOCUMENTS

| 4,177,107 | A | 12/1979 | Kumakura et al. |
| 4,193,845 | A | 3/1980 | Kaetsu et al. |
| 4,404,345 | A | 9/1983 | Janssen |
| 4,564,646 | A | 1/1986 | Nishigaki et al. |
| 5,037,435 | A | 8/1991 | Chang et al. |
| 5,278,201 | A | 1/1994 | Dunn et al. |
| 5,278,202 | A | 1/1994 | Dunn et al. |
| 5,324,519 | A | 6/1994 | Dunn et al. |
| 5,340,849 | A | 8/1994 | Dunn et al. |
| 5,487,897 | A | 1/1996 | Polson et al. |
| 5,599,552 | A | 2/1997 | Dunn et al. |
| 5,681,873 | A | 10/1997 | Norton et al. |
| 5,702,716 | A | 12/1997 | Dunn et al. |
| 5,733,950 | A | 3/1998 | Dunn et al. |
| 5,736,152 | A | 4/1998 | Dunn |
| 5,739,176 | A | 4/1998 | Dunn et al. |
| 5,744,153 | A | 4/1998 | Yewey et al. |
| 5,759,563 | A | 6/1998 | Yewey et al. |
| 5,780,044 | A | 7/1998 | Yewey et al. |
| 5,792,469 | A | 8/1998 | Tipton et al. |
| 5,945,115 | A | 8/1999 | Dunn et al. |
| 5,990,194 | A | 11/1999 | Dunn et al. |
| 6,143,314 | A | 11/2000 | Chandrashekar et al. |
| 6,261,583 | B1 | 7/2001 | Dunn et al. |
| 6,315,566 | B1 | 11/2001 | Shen et al. |
| 6,355,657 | B1 | 3/2002 | Osborne |
| 6,395,293 | B2 | 5/2002 | Polson et al. |
| 6,461,631 | B1 * | 10/2002 | Dunn et al. ................... 424/426 |
| 6,482,871 | B1 | 11/2002 | Aasen et al. |
| RE37,950 | E | 12/2002 | Dunn et al. |
| 6,528,080 | B2 | 3/2003 | Dunn et al. |
| 6,530,950 | B1 | 3/2003 | Alvarado et al. |
| 6,565,874 | B1 | 5/2003 | Dunn et al. |

(Continued)

FOREIGN PATENT DOCUMENTS

| EP | 1466631 | 10/2004 |
| HK | 1153675 | 5/2012 |

(Continued)

OTHER PUBLICATIONS

Southard et al. Exp. Opin. Invest. Drugs (1998) 7(9):1483-1491.*
"International Application Serial No. PCT/US2009/003361, Search Report mailed Oct. 27, 2010", 5.
"International Application Serial No. PCT/US2009/003361, Written Opinion mailed Oct. 27, 2010", 6.
Agnihotri, S A, et al., ""Novel interpenetrating network chitosan-poly(ethylene oXide-g-acrylamide) hydrogel microspheres for the controlled release of capecitabine"", International Journal of Pharmaceutics,Elsevier BV, NL—LNKDDOI:I0.I016/J.IJPHARM. 2006.05.061, vol. 324, No. 2, (Nov. 6, 2006), 103-115 Pages.

(Continued)

*Primary Examiner* — Janet Epps-Smith
(74) *Attorney, Agent, or Firm* — Mintz Levin Cohn Ferris Glovsky and Popeo, P.C.

(57) ABSTRACT

The invention provides a controlled release biodegradable polymer formulation adapted for administering bioactive agents such as therapeutic proteins to a patient through implantation of a bolus that forms a depot within the patient's body tissues. The formulation includes a dehydrated inclusion complex of the bioactive agent within a hydrogel, wherein the hydrogel can comprise a polymerized polyalkyleneglycolyl diacrylate, and, optionally, polyalkyleneglycolyl monoacrylates, including methacrylates. Alternatively, the hydrogel can comprise hyaluronic acid, chitosan, agarose, polyvinylacetate, polyvinylpyrrolide, or polyvinylalcohol nanoparticles. The bioactive agent can be a macromolecular material, such as a protein. A method of forming the inventive formulation is also provided, as well as a method for using the formulation in the treatment of a malcondition in a patient in need thereof.

11 Claims, No Drawings

(56) References Cited

U.S. PATENT DOCUMENTS

| | | | |
|---|---|---|---|
| 6,602,975 | B2 | 8/2003 | Hubbell et al. |
| 6,998,137 | B2 | 2/2006 | Shih et al. |
| 7,019,106 | B2 | 3/2006 | Yamamoto et al. |
| 7,060,299 | B2 | 6/2006 | Alavattan et al. |
| 7,115,691 | B2 | 10/2006 | Alvarado et al. |
| 2002/0192294 | A1 | 12/2002 | Albayrak |
| 2006/0264571 | A1 | 11/2006 | Siol |

FOREIGN PATENT DOCUMENTS

| | | | |
|---|---|---|---|
| WO | WO-9527481 | A1 | 10/1995 |
| WO | WO-2004011054 | A2 | 2/2004 |
| WO | WO-2007083870 | A1 | 7/2007 |
| WO | WO2007083870 | A1 * | 7/2007 |
| WO | WO 2009073193 | A2 * | 6/2009 |
| WO | WO-2009148579 | A2 | 12/2009 |

OTHER PUBLICATIONS

Jarr, et al., ""Sustained release of lidocaine from an injectable implant system for treatment of post-operative Pain"", Proceedings of the International Symposium on Controlled Release Bioactive Materials, Controlled Release Society, vol. 26, (Jul. 1, 1999), 631/632 pages.

Lambert, W J, et al., ""Development of an In Situ Forming Biodegradable Poly-Lactide-Co- Glycolide System for the Controlled Release of Proteins"", Journal of Controlled Release, Elsevier, Amsterdam LNKDDOI: DI0.1016/0168-3659(94)00083-7, vol. 33, No. 1, (Jan. 1, 1995), 189-195.

Liu, Y, et al., ""Synthesis, properties and controlled release behaviors of hydrogel networks using cyclodextrin as pendant groups"", Biomaterials, Elsevier Science Publishers BV., Barking, GB LNKDOI-I0.I016/J.Biomaterials.2005.04.011, vol. 26, No. 32, (Nov. 1, 2005), 6367-6374.

Singh, M, et al., ""Controlled release of LHRH-DT from bioerodible hydrogel microspheres"", International Journal of Pharmaceutics Elsevier BV, NL LNKDDOI-I0.I016/0378-5173(91)90283-T, vol. 76, No. 3, (Oct. 15, 1991).

"European Application Search No. 09758743.0, Office Action mailed Jan. 17, 2011", 2 pgs.

"European Application Search No. 09758743.0, Response filed Feb. 28, 2011 to Office Action mailed Jan. 17, 2011", 18 pgs.

"International Application Serial No. PCT/US2009/003361, International Preliminary Report on Patentability mailed Dec. 16, 2010", 6 pgs.

De Ascentiis, A., et al., "Mucoadhesion of poly(2-hydroxyethyl methacrylate) is improved when linear poly(ethylene oxide) chains are added to the polymer network", *Journal of Controlled Release*, 33(1), (1995), 197-201.

Diramio, J. A., et al., "Poly(ethylene glycol) Methacrylate/Dimethacrylate Hydrogels for Controlled Release of Hydrophobic Drugs", *Biotechnol. Prog.*, 21, (2005), 1281-1288.

Ficek, B. J., et al., "Novel preparation of poly(vinyl alcohol) microparticles without crosslinking agent for controlled drug delivery of proteins", *Journal of Controlled Release*, 27, (1993), 259-264.

Lee, J. H., et al., "Protein-resistant surfaces prepared by PEO-containing block copolymer surfactants", *Journal of Biomedical Materials Research*, 23(3), (Mar. 1989), 351-368.

Li, J. K., et al., "Poly(vinyl alcohol) nanoparticles prepared by freezing-thawing process for protein/peptide drug delivery", *Journal of Controlled Release*, 56, (1998), 117-126.

Mellott, M. B., et al., "Release of protein from highly cross-linked hydrogels of poly(ethylene glycol) diacrylate fabricated by UV polymerization", *Biomaterials*, 22, (2001), 929-941.

Scott, R. A., et al., "Highly crosslinked, PEG-containing copolymers for sustained solute delivery", *Biomaterials*, 20, (1999), 1371-1380.

Takamura, A., et al., "Drug release from poly(vinyl alcohol) gel prepared by freeze-thaw procedure", *Journal of Controlled Release*, 20, (1992), 21-28.

Wang, N., et al., "A Heterogeneously Structured Composite Based on Poly(lactic-co-glycolic acid) Microspheres and Poly(vinyl alcohol) Hydrogel Nanoparticles for Long-Term Protein Drug Delivery", *Pharmaceutical Research*, 16(9), (1999), 1430-1435.

Zhao, X., et al., "Novel Degradable Poly(ethylene glycol) Hydrogels for Controlled Release of Protein", *Journal of Pharmaceutical Sciences*, 87(11). (1998), 1450-1457.

* cited by examiner

DEHYDRATED HYDROGEL INCLUSION COMPLEX OF A BIOACTIVE AGENT WITH FLOWABLE DRUG DELIVERY SYSTEM

CROSS-REFERENCE TO RELATED APPLICATIONS

This application is a nationalization under 35 U.S.C. 371 of PCT/US2009/003361, filed Jun. 3, 2009 and published as WO 2009/148579 A1on Dec 10, 2009, which claims priority to U.S. Provisional Application Ser. No. 61/058,484, filed Jun. 3, 2008, which applications are incorporated herein by reference in its entirety.

FIELD OF INVENTION

The invention relates to a composition adapted for controlled release of a bioactive agent from a depot implanted within the body tissues of a patient, wherein the bioactive agent is included within a matrix of a dehydrated hydrogel; the complex of the bioactive agent and the hydrogel being further incorporated into a controlled release formulation that includes a biodegradable polymer and an organic solvent.

BACKGROUND

Copolymer compositions adapted for use in controlled release delivery systems such as biodegradable and bioerodible implants are known. See, for example, U.S. Pat. Nos. 7,019,106; 6,565,874; 6,528,080; RE37,950; 6,461,631; 6,395,293; 6,355,657; 6,261,583; 6,143,314; 5,990,194; 5,945,115; 5,792,469; 5,780,044; 5,759,563; 5,744,153; 5,739,176; 5,736,152; 5,733,950; 5,702,716; 5,681,873; 5,599,552; 5,487,897; 5,340,849; 5,324,519; 5,278,202; and 5,278,201. Such controlled release systems are in general advantageous because they provide for the controlled and sustained release of medications, often directly at or near the desired site of action, over the period of days, weeks or even months. Controlled release systems can include polymer matrices that are known to be broken down in the body by various endogenous substances such as enzymes and body fluids, such as polyesters including poly-lactide, poly-glycolide, and copolymers thereof ("PLG copolymers") prepared from glycolide (1,4-dioxan-2,5-dione, glycolic acid cyclic dimer lactone) and lactide (3,6-dimethyl-1,4-dioxan-2,5-dione, lactic acid cyclic dimer lactone), or from glycolate (2-hydroxyacetate) and lactate (2-hydroxypropionate). These copolymer materials are particularly favored for this application due to their facile breakdown in vivo by body fluids or enzymes in the body to non-toxic materials, and their favorable properties in temporally controlling the release of medicaments and biologically active agents ("bioactive agents") that may be contained within a mass of the controlled release formulation incorporating the polymer that has been implanted within a patient's body tissues. Typically, controlled release systems are adapted to provide for as constant a rate of release as possible of the bioactive agent over the time period that the implant persists within the body.

Flowable delivery systems, such as the Atrigel® system, are disclosed in U.S. Pat. Nos. 6,565,874, 6,528,080, 6,461,631, 6,395,293, and references found therein. Flowable delivery systems like the Atrigel® system include a biodegradable polymer, a bioactive agent, and an organic solvent that has at least a very slight solubility in body fluids. When the substantially liquid ("flowable") solution of the delivery system is injected into a patient's tissues, typically as a single bolus, the organic solvent diffuses into surrounding body fluids, causing precipitation or gelation of the water-insoluble polymer containing the bioactive agent. It is believed that initially a "skin" forms on the deposited liquid mass, bringing about formation of the semi-solid deposit known as a depot that contains the remaining solution of the polymer and the bioactive agent in the solvent. As the depot resides in the tissues, the solvent continues to diffuse out and body fluids continue to diffuse in, bringing about ongoing precipitation of the polymer with the bioactive agent, until a gelled or solid mass remains. Channels or pores may form in the depot as part of this process. Due to the biodegradable nature of the polymer in the presence of body fluids and of enzymes within the body, the polymer slowly degrades into soluble non-toxic hydrolysis products, releasing the contained bioactive agent over a period of time. This process continues until the depot is substantially completely dissolved and all the bioactive agent is released. It is understood that such depots can be adapted to persist for various lengths of time within the body, such as about 30 days, about 60 days, or about 3 months, 4 months, or 6 months.

Polyalkyleneglycols, such as polyethyleneglycol, are well known substances formed by the polymerization of alkylene oxides, such as ethylene oxide. Despite their often high molecular weights, ranging up into the hundreds of thousands, and their non-ionic nature, they tend to have a high degree of solubility in water due to the abundance of oxygen atoms in their structures, which are available to enter into hydrogen bonding interactions with water molecules. Polyethyleneglycol groups are known to interact with proteins with minimal irreversible absorption of the protein by the polyethyleneglycol (J H Lee, J Kopecek, J D Andrade (1989), *J. Biomed. Mater. Res.*, 23, 351-368). Thus, polyethyleneglycols are also known to interact with proteins in beneficial ways, such as to stabilize native forms through hydrogen bonding which serves to help resist denaturation of the protein.

Polyethyleneglycols can be prepared as linear chains, or, by incorporation of multifunctional initiators such as pentaerythritol, can be prepared in non-linear configurations. Linear polyethyleneglycols and other polyalkyleneglycols (e.g., polypropyleneglycols) contain two terminal hydroxyl groups per molecular chain, which are available for chemical bonding, for example with carboxylic acids to form esters. One such group of esters that are well known are the polyethyleneglycol diacrylates, which include diesters of polyethyleneglycol (PEG) with unsubstituted acrylic acid (prop-2-enoic acid) and methacrylic acid (2-methyl-prop-2-enoic acid). These PEG diesters, being acrylates, can themselves undergo polymerization via the acrylate groups to provide ladder-type polymers which can be viewed as at least two or, most likely, many polyacrylate chains cross-linked by the polyethyleneglycol chains. Since a number of different polyacrylate chains can all be crosslinked by the polyethyleneglycol chains and thus all covalently connected to each other, it is believed that the polyethyleneglycolyl polyacrylates have highly three-dimensional structures.

Such materials have been used in a variety of applications, for example, as components of contact lenses (U.S. Pat. No. 5,037,435 and U.S. Pub. No. 2006/0264571), adhesives (U.S. Pat. Nos. 4,404,345 and 6,482,871), electrical insulating resins (U.S. Pat. No. 4,564,646), and dental materials (U.S. Pat. No. 6,315,566); for immobilization of cells and enzymes (U.S. Pat. Nos. 4,177,107 and 4,193,845), and for stent coatings (U.S. Pat. Nos. 6,530,950 and 7,115,691). The polyethyleneglycol diacrylates have also been used for formation of hydrogels containing bioactive compounds for the purpose of drug delivery, including small molecule drugs (R A Scott, N A Peppas (1999), *Biomaterials,* 20, 1371-1380; J A Diramio et al. (2005), "Poly(ethylene glycol) methacrylate/dimethacrylate hydrogels for controlled release of hydrophobic drugs," *Biotech Prog.,* 21(4), 1281-8). Polymer compositions formed of polyethyleneglycol polyacrylates wherein poly-glycolic acid segments are covalently bonded within the structure have been studied as for controlled release applications (U.S. Pat. No. 6,602,975). Proteins have been covalently cross-linked to hydrogels formed by polymerization of polyethyleneglycol diacrylates and their rates of release studied (M B Mellott, K Searey, M V Pishko (2001), *Biomaterials,* 22, 929-941). However, without such covalent bonding of the protein to the polyethyleneglycol polyacrylate framework, long-term controlled release is not observed, as the protein can freely diffuse out of the framework, which does not strongly bind the protein through non-covalent interactions (X Zhao, J M Harris, (2000), *J. Pharm. Sci.,* 87(11), 1450-1458).

Various components have been added to stabilize proteins in formulations against aggregation and formation of unnatural conformations. The use of a naturally occurring polysaccharide as a stabilizer for a protein, encapsulated with a biodegradable polymer, is discussed in U.S. Pat. No. 7,060,299. U.S. Pat. No. 6,998,137 discusses biodegradable polymers including proteins precipitated on sparingly soluble particles, wherein the sparingly soluble particle is selected from the group consisting of zinc carbonate, zinc oxide, zinc tartrate, zinc hydroxide, zinc phosphate, zinc citrate, magnesium oxide, magnesium hydroxide, magnesium carbonate, calcium oxide, calcium phosphate, calcium sulfate, and calcium carbonate.

SUMMARY OF THE INVENTION

The present invention is directed to controlled release formulations adapted for release of a bioactive agent, the formulations comprising a dehydrated complex of the bioactive agent in a hydrogel in combination with a biodegradable polymer and a solvent; as well as methods for preparing, and methods for using the inventive controlled release formulation.

Various embodiments of the invention provide controlled release formulations adapted for release of a bioactive agent in body tissue, the formulation comprising a biodegradable polymer, an organic solvent that is at least slightly soluble in body fluids, and a dehydrated inclusion complex of the bioactive agent within a hydrogel. In some embodiments, the biodegradable polymer is a biodegradable polyester. In some embodiments the biodegradable polymer is a biodegradable poly(lactide-glycolide) (PLG) copolymer. In various embodiments the hydrogel comprises a polymerized polyalkyleneglycolyl diacrylate or a copolymerized polyalkyleneglycolyl diacrylate and polyalkyleneglycolyl monoacrylate. The polyalkyleneglycolyl groups can be polyethyleneglycolyl or polypropyleneglycolyl groups.

In various embodiments, the bioactive agent is a macromolecular substance, for example, a protein such as a monoclonal antibody, or a nucleic acid. In other embodiments the bioactive agent is a small molecule substance, such as a peptide or an organic compound of molecular weight less than about 1,000 Da.

An inclusion complex of a bioactive agent within a hydrogel, when dehydrated, can be incorporated into a controlled release formulation of the "Atrigel®" type that includes a biodegradable PLG copolymer and an organic solvent that dissolves the copolymer and is at least slightly soluble in an aqueous medium. The protein can be released from the hydrogel in undenatured or native form. The hydrogels can be composed of polymerized polyalkyleneglycolyl diacrylate and the copolymerized polyalkyleneglycolyl diacrylate and polyalkyleneglycolyl monoacrylate, both referred to herein as polyalkyleneglycolyl polyacrylates, that upon hydration form hydrogels. When an embodiment of the inventive formulation is implanted, for example as a depot, within the body tissues of a patient, and the dehydrated hydrogel inclusion complex is consequently exposed to body fluids through biodegradation of the Atrigel® type polymer depot, the dehydrated hydrogel inclusion complex rehydrates and can slowly release the protein into the body fluids such that it enters the circulatory system of the patient.

Various embodiments of the present invention concern methods of preparing an inventive controlled release formulation comprising a dehydrated complex of a bioactive agent and a hydrogel, dispersed in a solution of a biodegradable polymer in an at least slightly water-soluble organic solvent. In some embodiments, the biodegradable polymer is a biodegradable polyester. In some embodiments the biodegradable polymer is a biodegradable PLG copolymer. The bioactive agent can be a macromolecular substance, or it can be a small molecule substance. A hydrated inclusion complex of the bioactive agent can be formed by contacting the bioactive agent and a hydrogel in an aqueous medium. A dehydrated inclusion complex can be formed by drying the hydrated inclusion complex, for example by a process involving lyophilization. This dehydrated inclusion complex can then be dispersed in a solution of the polymer in the organic solvent. The dehydrated inclusion complex of the bioactive agent in the hydrogel can, for example, be in the form of microparticles or nanoparticles, or more generally in the form of a finely powdered solid. For example, a polyalkyleneglycolyl diacrylate can be polymerized in an aqueous medium and the bioactive agent added to provide a hydrogel containing the bioactive agent as the hydrated inclusion complex. This combination can then be dehydrated, such as by lyophilization, to provide a dehydrated inclusion complex of the bioactive agent in the polyalkyleneglycolyl polyacrylate in the form of microparticles or nanoparticles, or more generally in the form of a finely powdered solid. In various embodiments, the polyalkyleneglycolyl diacrylate can be polymerized, or the polyalkyleneglycolyl diacrylate and the polyalkyleneglycolyl monoacrylate can be copolymerized, wherein the polymerization reaction is initiated with UV light, or with an initiator material, or with both.

The invention further concerns a method of treatment of a malcondition for which the bioactive agent, such as a macromolecular substance, is effective. The method involves administering the inventive controlled release formulation including the dehydrated hydrogel inclusion complex of the bioactive agent that is medically indicated for treatment, prevention, or palliation of the malcondition, in combination with a biodegradable polymer and an organic solvent, to a patient in need thereof, at a dosage level and for a duration effective to treat, prevent, or palliate the malcondition.

In some embodiments, the controlled release formulation described herein is used in the manufacture of a medicament for treatment of a malcondition, wherein the formulation includes a bioactive agent that is medically indicated for treatment, prevention, or palliation of the malcondition.

DETAILED DESCRIPTION

Definitions

A "controlled release formulation," as the term is used herein, is a composition including a bioactive agent, that is adapted to release the bioactive agent, which is useful in treating a malcondition in a patient, over a prolonged period of time, at a defined rate of release. The controlled release formulation can be introduced into the body tissues of the patient as a single injected bolus, or "depot," which is adapted to slowly biodegrade, such as through the action of enzymes and body fluids, and to release the bioactive agent into the patient's body fluids as the depot biodegrades. In the invention herein, the bioactive agent is present as a dehydrated inclusion complex of the agent in a hydrogel, which is included (dispersed) in a solution of a biodegradable polymer in an organic solvent that is at least slightly soluble in body fluids.

An "organic solvent at least slightly soluble in body fluids" is an organic solvent that can be completely water-soluble, or can have a low degree of water-solubility, provided that it is sufficiently soluble in aqueous body fluids to allow for at least slow removal over time of some fraction of the solvent from the implanted depot. It is understood that materials that may be insoluble in pure water nevertheless have some at least limited solubility in body fluids, due to the presence of additional components, such as proteins and the like, in the body fluids that assist in carrying away the solvent molecules.

A "bioactive agent" refers to a molecular substance or a combination of molecular substances, which can include a macromolecular substance such as a protein or a nucleic acid, or a "small molecule" substance, such as a peptide or an organic compound of a molecular weight less than about 1,000 Da, that can be used to treat, prevent, or palliate a disease or malcondition in a patient. Examples of bioactive agents include octreotide citrate, leuprolide acetate, small interfering RNAs, insulin, human growth hormone, and monoclonal antibodies such as cetuximab (Erbatux®) and bevacizumab (Avastin®).

As the term is used herein, an "acrylate" is a derivative of acrylic acid, including substituted acrylic acid derivatives such as methacrylic acid derivatives (specifically termed "methacrylates" when that particular acrylate is referred to), as well as other α- and β-substituted acrylates bearing substituents on the vinyl carbon atoms. Thus "acrylates" include compounds with structures as shown:

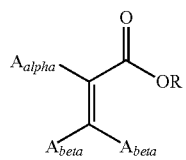

When $A_{alpha}$ and $A_{beta}$ are all hydrogen atoms, the structure represents an unsubstituted acrylate. When $A_{alpha}$ is methyl and both $A_{beta}$ are hydrogen, the structure represents a methacrylate. It is understood that any of the $A_{alpha}$ or $A_{beta}$, can be alkyl groups, substituted or unsubstituted, within the meaning of "acrylate" herein. In the acrylates of the present invention, R is an polyoxyalkyleneglycolyl group, which can bear a second acrylate at the distal terminus of the polyoxyalkyleneglycol chain. When the polyoxyalkyleneglycol group is a polyethyleneglycol group, bearing a second acrylate ester at its distal end (termed a "polyoxyalkyleneglycolyl diacrylate"), the molecular weight of the polyethyleneglycol moiety can range between about 500 Da and about 10,000 Da (degree of polymerization about 12 to about 2,500). When the distal end of the polyethyleneglycol moiety is not esterified (termed a "polyoxyalkyleneglycolyl monoacrylate"), the moiety can be a monomeric ethylene glycol ester of the acrylate (hydroxyethylmethacrylate) or the polyoxyalkyleneglycol moiety can range up to a degree of polymerization of about 12 (MW about 500 Da). As used herein, "Da" is an abbreviation of "dalton", a unit of molecular weight as is well known in the art. The term "kDa" refers to kilodalton, a unit equaling 1,000 daltons.

A "polyalkyleneglycol" or a "polyalkyleneglycolyl" compound refers to a polymer formed of monomeric units containing carbon and oxygen atoms, wherein the oxygen atoms are separated by two, three, or more carbon atoms; as shown below wherein n is two or more and m can range from one up into the hundreds or even thousands of repeating units.

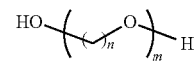

Thus, as m can range upwards from a value of one, a mono-alkyleneglycol is defined as a polyalkyleneglycol within the meaning herein; for example, an ethyleneglycol monoacrylate (hydroxyethylacrylate) or diacrylate (e.g., bis-acryloylethyleneglycol) is a polyethyleneglycol monoacrylate or diacrylate within the meaning herein. The number of carbon atoms in each repeating unit, n, is two or greater.

As is well known, polyalkyleneglycols can be prepared through the polymerization of alkylene oxides. For example, a polyalkyleneglycol group can be a polyethyleneglycol group:

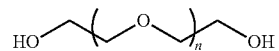

which can readily be prepared by polymerization of ethylene oxide.

Thus, an example of a polyalkyleneglycolyl diacrylate as the term is used herein is a polyethyleneglycolyl dimethacrylate:

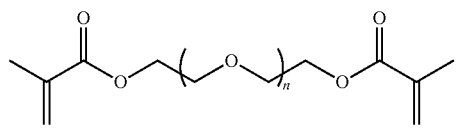

wherein n can range from about two up into the hundreds or thousands. This class of structures are termed "PEG diacrylate" or "PEG diacrylate monomer" and if the acrylates are specifically methacrylates, "PEG dimethacrylate" or "PEG dimethacrylate monomer".

An example of a polyalkyleneglycol monoacrylate as the term is used herein is hydroxyethyl mono-methacrylate, also known as hydroxyethyl methacrylate:

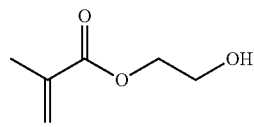

Another example is diethyleneglycol mono-methacrylate, also known as diethyleneglycol methacrylate. This class of structures are generally termed "PEG monomethacrylates".

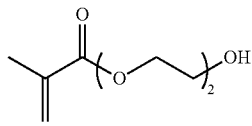

When the "polymerization" of a polyalkyleneglycolyl diacrylate or dimethacrylate is referred to herein, polymerization of the acrylate (methacrylate) groups is indicated, as is well known in the art. This polymerization results in formation of carbon chains bearing pendant carboxyl groups forming ester bonds with the polyethyleneglycol groups. The product can be viewed as a plurality of polyacrylate (polymethacrylate) chains with inter-chain crosslinks formed by polyethyleneglycol chains. As such, it makes up a multi-dimensional structure rather than a one-dimensional chain as is typical of linear polymers. This multi-dimensional structure is referred to herein as a polyalkyleneglycolyl polyacrylate or a PEG-polyacrylate, for example, as a polyethyleneglycolyl polymethacrylate (PEG-polymethacrylate) when the polyalkyleneglycol is polyethyleneglycol and the acrylate is methacrylate. The multi-dimensional structure can also be referred to as a "polymerized polyalkyleneglycolyl diacrylate." These substances are also referred to as "hydrogels" and "hydrogel forming materials" of the invention.

It is understood that when a PEG diacrylate monomer undergoes polymerization, polyacrylate chains are formed, but any covalently connected PEG polyacrylate molecule can, and is believed to, include more than just two polyacrylate chains, as polymerizing acrylate groups can join any growing chain and are not restricted to always at each step of acrylate incorporation joining the same chain. Therefore, it is believed that the polymerized PEG diacrylate or the copolymerized PEG diacrylate/PEG monoacrylate materials of the invention possess highly three-dimensional structures wherein many individual polyacrylate backbones are interconnected via the PEG chains.

When copolymerization of a PEG monoacrylate with a PEG diacrylate takes place, PEG groups with a free end are incorporated into the copolymer. As the monoacrylate molecules have no second acrylate group for another chain to incorporate, the PEG group in this case is believed to bear a terminal hydroxyl group.

A "hydrogel" as the term is used herein refers to a hydrogel forming material, or the gel formed by contacting the hydrogel forming material and an aqueous medium. A hydrogel is a three-dimensional network of crosslinked hydrophilic polymers or copolymers that can swell, but not dissolve, in an aqueous medium such as water. (Peppas and Mikos, "Preparation Methods and Structure of Hydrogels", *Hydrogels in Medicine and Pharmacy*, v. 1 (1986)). Crosslinking can be physical (for example, by hydrogen bonding) or chemical (for example, by covalent bonding). An example of a hydrogel forming material is a polyalkyleneglycolyl polyacrylate of the invention, which when exposed to an aqueous milieu forms a hydrated or rehydrated hydrogel. In the presence of water, the hydrophilic polyalkyleneglycol chains are hydrated by water molecules and the structure swells with water to form a semi-solid material. The hydrogel so formed can include other substances, for example proteins, forming inclusion complexes wherein the substances, particular macromolecular substances such as proteins, are held by non-covalent interactions, such as by hydrogen bonds or van der Waals interactions. Other examples of hydrogels include those formed by natural polymers such as hyaluronic acid, chitosan or agarose, or by synthetic polymers such as those formed by polymerization of vinyl acetate or N-vinyl-2-pyrrolidone. Hydrogel materials can also be formed from polyvinylalcohol nanoparticles formed by a freeze-thaw process (Takamura, et al (1992), *Journal of Controlled Release*, 20, 21-28; Ficek and Peppas (1993), *Journal of Controlled Release*, 27, 259-263; Wang, et al. (1999), *Pharmaceutical Research*, 16(9), 1430-1435; Li, et al. (1998), *Journal of Controlled Release*, 56, 117-126).

When a hydrogel is dried, the material obtained is a hydrogel forming material. When a hydrogel is mixed with an included substance, such as a protein, and then is dehydrated, the resulting product is termed an "inclusion complex" or a "dehydrated inclusion complex." A hydrogel containing a bioactive substance such as a protein can be dried by standard means such as lyophilization to provide a dried powder, or can be dried with formation of microparticles or microspheres, to yield the inclusion complex in microparticulate form.

A "biodegradable polymer" as the term is used herein refers a polymer that undergoes depolymerization at a finite or significant rate under conditions found in body tissue, for example the presence of body fluids or hydrolytic enzymes. A biodegradable polymer as the term is used herein is not substantially water-soluble in intact form, but upon hydrolysis or other type of depolymerization produces monomers or other breakdown units that have at least some solubility in water, such that a depot of the biodegradable polymer in body tissue is ablated over time by the action of endogenous body tissue constituents. Examples of biodegradable polymers which can be used in this application include certain polyesters, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids) and copolymers, terpolymers, or combinations or mixtures of the above materials.

A "PLG copolymer" as used herein refers to a poly (lactide-glycolide) polymer formed of monomeric lactide (or lactate) and glycolide (or glycolate) units in a defined molar proportion joined by ester bonds. The molar proportion can range from 100 mole % lactide to 100 mole % glycolide but typically ranges from about 50-100 mole % lactide. Thus, a pure poly(lactide), i.e., 100 mole % lactide, also known as PLA, is a PLG copolymer within the meaning herein. Copolymers composed of both lactide and glycolide units can be described in terms of their molar compositions; i.e., a 65/35 PLG is understood to consist of 65 mole % lactide units and 35 mole % glycolide units. A copolymer can include neutral poly(lactide-glycolide) molecular chains that terminate in alcohol or ester groups, or ionic poly (lactide-glycolide) molecular chains that terminate in carboxylic acid groups (also referred to as PLGH copolymers). PLG copolymers as the term is used herein include compositions referred to in the art as poly(lactate-glycolate), poly (lactate(co)glycolate), poly(lactide-glycolide), poly(lactide (co)glycolide), and the like, with the understanding that additional moieties may be included, such as core or initiator groups (for example, diols, hydroxyacids, and the like), capping groups (for example, esters of terminal carboxyl groups, and the like) and other pendant groups or chain extension groups covalently linked to or within the polyester backbone, including groups that cross-link the substantially linear polyester molecular chains.

Methods of preparation of these various types of PLG copolymer are well known in the art; for example a neutral PLG can be synthesized by catalyzed polymerization of lactide and glycolide reagents (cyclic dimers) from a core diol, such as hexane-1,6-diol, wherein ester bonds are formed between the end of the growing chains and the newly added lactide/glycolide units resulting in polymer chains wherein both ends have terminal hydroxyl groups, which are neutral. Alternatively, an ionic or acidic PLG (a PLGH) can be prepared by polymerization of lactide/glycolide reagents initiated by lactic acid, wherein one end of the PLG chain that is formed bears an ionizable carboxylic acid group. An acidic PLGH can be capped with an alcohol, that is, an ester group can be formed from the free carboxylic end group and the alcohol, to provide a neutral PLG copolymer within the meaning herein.

The terms "burst effect" or "initial burst effect" are used herein to refer to the situation in which a higher than average rate of diffusion of a bioactive agent out of a controlled release formulation occurs immediately following emplacement of a liquid delivery system, for example, within 1-2 days following emplacement. By "higher than average" is meant that during this initial time period following emplacement of the controlled release formulation with body tissues, the rate of release of the agent is higher than is seen on the average over the entire period of time that the implant continues to release the agent within the body tissues. Thus a burst effect represents a surge of the bioactive agent, which can amount to 25-30% of the total agent contained in the depot, immediately after emplacement that tapers off to the lower rate of release that occurs throughout the total time period that the depot persists within the body tissues. A "low burst copolymer" is a copolymer that, when incorporated into a controlled release formulation, for example of the Atrigel® type, provides for a low initial burst effect and avoids the undesired effects on the patient of a transient but high level of the bioactive agent immediately following emplacement of the depot.

One type of low burst copolymer, referred to herein as a "PLG(p) copolymer," is a PLG copolymer adapted for use in a controlled release formulation characterized by a weight average molecular weight of about 10 kilodaltons to about 50 kilodaltons and a polydispersity index of about 1.4 to about 2.0, and having separated therefrom a copolymer fraction characterized by a weight average molecular weight of about 4 kDa to about 10 kDa and a polydispersity index of about 1.4 to about 2.5. As is disclosed in U.S. Ser. No. 60/901,435 by the inventors herein, this PLG low-burst copolymer material can be prepared by dissolving a starting PLG copolymer material, which is not a product of hydrolysis of a higher molecular weight PLG copolymer material, in a solvent, then precipitating the low-burst copolymer material with a non-solvent. A PLG(p) copolymer can be a component of a constant release copolymer as disclosed and claimed herein.

A "molecular weight" as the term is used herein with respect to polymers refers to a weight average molecular weight as is well known in the art, when the reference is to a composition made up of individual molecules having a range of molecular weights, as in the case of PEG moieties, PEG esters, and biodegradable polymers including PLG copolymers. When referring to a homogeneous composition such as a single molecular species, molecular weight refers to the exact molecular weight of the species in question.

DETAILED DESCRIPTION

The invention provides a controlled release formulation adapted for release of a bioactive agent such as a protein or a small molecule medicinal compound over a period of time within the body tissues of a patient in need thereof. The formulation contains a biodegradable polymer, an organic solvent that is at least slightly soluble in body fluids, and a dehydrated inclusion complex of the bioactive agent within a hydrogel. The biodegradable polymer can be formed of a biodegradable polyester such as a biodegradable PLG copolymer. The hydrogel can be formed of polymerized polyalkyleneglycolyl diacrylate or a copolymerized polyalkyleneglycolyl diacrylate and polyalkyleneglycolyl monoacrylate (both being referred to herein as a polyalkyleneglycolyl polyacrylate). Alternatively, the hydrogel can comprise hyaluronic acid, chitosan, agarose, polyvinylacetate, polyvinylpyrrolide, or polyvinylalcohol nanoparticles.

In various embodiments the bioactive agent is a macromolecular substance, such as a protein, e.g., a monoclonal antibody, or a nucleic acid, e.g., a small interfering RNA. An example of a macromolecular bioactive agent is insulin. Another example is human growth hormone. Another example is an anticancer monoclonal antibody, such as cetuximab (Erbatux®), or bevacizumab (Avastin®). It is believed that by formation of an inclusion complex of the bioactive agent such as a protein within the matrix of a hydrogel, such as polyalkyleneglycolyl polyacrylate, the protein is stabilized and aggregation and denaturation are minimized. Thus, through formation of the inventive inclusion complex, the protein is more effectively kept in its native configuration during the process of forming, storing and administering the controlled release formulation containing the protein. Aggregation of proteins can not only cause loss of desired bioactivity, but can also cause the immune system of a patient to mount a response which can result in undesirable anaphylactic responses upon administration of the protein to the patient. This may also be true of macromolecular nucleic acid materials, such as small interfering ribonucleic acids (siRNAs).

The multidimensional polymer network of the hydrogel, for example the network formed by the polymerization/copolymerization process of the polyalkyleneglycolyl diacrylate and, optionally, monoacrylate, serves to provide a molecular environment wherein the protein molecules are kept separate from each other and where the protein molecules do not strongly adhere to the polymer molecules that surround them in the matrix. It is understood that the protein is not covalently linked to this matrix; therefore degradation of the matrix may not be required for release of the protein once the matrix containing the protein is re-hydrated in the body. No covalent bond between the protein and the polyalkylenglycolyl polyacrylate matrix need be cleaved for release of the protein. Indeed, without inclusion of the complex into a formulation that provides for sustained release, it is believed that in general the protein would be released from the inclusion complex, once hydrated, more rapidly than would be desired for sustained release.

In order to sustain or prolong the release of the bioactive agent, e.g., protein, over medically useful periods of time, such as weeks or months, the inclusion complex of the agent in the multidimensional polymer matrix is contained within a mass of a second type of polymer adapted to provide for controlled release. The second type of polymer may be a biodegradable polymer, a biodegradable polyester, or a biodegradable poly(lactide-glycolide) copolymer, as described above. In some embodiments, these copolymer ester bonds are subject to hydrolysis within the body tissues of a patient through the action of enzymes and body fluids, such that the biodegradation brings about slow release of lactate and glycolate into the body fluids and results in erosion of the PLG copolymer. This erosion results in release of the dehydrated inclusion complex of the agent within the hydrogel, e.g., polyalkyleneglyolyl polyacrylate matrix, from which matrix the agent is relatively rapidly released into the body fluids. Biodegradation of the polyacrylate may occur during and after the release of the protein, but as the protein is not strongly hydrogen-bonded by the matrix, and is not covalently linked to the matrix, biodegradation of the polyacrylate need not occur for the protein release to take place.

The inventive formulation further contains an organic solvent that is at least very slightly soluble in body fluids, that is, body fluids that are aqueous but also include other components, can carry away molecules of the organic solvent from the depot implant site over time. The organic solvent can preferably be fully soluble in the body fluids, for example, N-methylpyrrolidone. The organic solvent dissolves the biodegradable polymer of the formulation, and serves to disperse the inclusion complex of the macromolecular substance within the polyacrylate matrix. Preferably, the inclusion complex does not dissolve or swell in the organic solvent, as this could result in premature release of the protein or other macromolecule from the matrix, causing denaturation or aggregation. Examples of organic solvents that can be used include N-methylpyrrolidone, dimethylacetamide, dimethylformamide, dimethylsulfoxide, or a polyethyleneglycol.

The inventive controlled release formulation includes the dehydrated inclusion complex of the bioactive agent in the polyacrylate matrix, the biodegradable polymer such as PLG copolymer, and the organic solvent. The invention provides a method of preparing this controlled release formulation by first polymerizing the polyalkylenglycolyl diacrylate or copolymerizing the polyalkylenglycolyl diacrylate and the polyalkylenglycolyl monoacrylate in a first aqueous medium to provide a hydrogel, optionally dehydrating the hydrogel, then contacting the hydrogel material with the bioactive agent in a second aqueous medium to form a hydrated inclusion complex, then dehydrating the hydrated inclusion complex to provide a dehydrated inclusion complex, and lastly dispersing the dehydrated inclusion complex in a solution of the biodegradable polymer in the organic solvent.

The polymerization of the polyalkylenglycolyl diacrylate or the copolymerization of the polyalkylenglycolyl diacrylate and the polyalkylenglycolyl monoacrylate in the first aqueous medium to provide a hydrogel can take place using a range of concentrations of the PEG diacrylate monomer and, optionally, the PEG monoacrylate monomer. The concentration can be as low as about 5 wt % in the aqueous medium, or can be up to about 50 wt % in the aqueous medium. Although the PEG diacrylate and PEG monoacrylate monomers have a high degree of water solubility, cosolvents can be present in the polymerization reaction, for example, ethanol can be used.

The molecular weight, that is, weight average molecular weight, of the polyalkyleneglycolyl diacrylate used in formation of the hydrogel, can vary depending upon the molecular weight of the bioactive agent that is to be contained within the dehydrated inclusion complex. In general, the higher the molecular weight of the bioactive agent, the higher the molecular weight of the hydrogel-forming monomer, i.e., PEG diacrylate monomer, that can preferably be polymerized into a suitable matrix for the bioactive agent. For example, for a peptide of molecular weight about 1000, a PEG diacrylate monomer of molecular weight about 700 Da can be used. If the PEG diacrylate monomer is a PEG dimethacrylate, the molecular weight of the two methacrylate moieties makes up about 140 Da, so the molecular weight of the constituent PEG moiety is about 550.

The polymerization or copolymerization of the PEG diacrylate or diacrylate plus monoacrylate, termed herein the "polymerization reaction," can be carried out by any suitable means known in the art, but preferably the polymerization reaction is initiated by the use of ultraviolet (UV) light. Preferably an initiator adapted for activation by UV light is included at an appropriate concentration in the aqueous medium, for example at a concentration of about 0.1 wt %. An example of an initiator suitable for use is 1-[4-(2-hydroxyethoxy)-phenyl]-2-hydroxy-2-methyl-1-propan-1-one (Irgacure 2959). Illumination of the aqueous solution of the monomers and preferably the initiator, for example with UV light of a wavelength of about 365 nm, results in the polymerization of the PEG acrylate monomers and the formation of a hydrogel. The hydrogel is a material of semi-solid texture, having undergone the transition from sol to gel through formation of the multidimensional matrix containing the aqueous medium. The UV illumination of the monomer solution can take place where the solution is in an appropriate physical configuration, such as a relatively thin layer, enabling even penetration of the light. For example, the solution can be placed in a tray to a relatively thin depth, such as about 1-10 mm, and then illuminated with a UV source of appropriate intensity. Preferably, steps are taken to avoid contamination, such as bacterial growth, through the use of suitable sterile techniques.

It is understood that a person of ordinary skill in the art can select a UV activated initiator and an illumination wavelength suitable to give a desired degree of polymerization without undue experimentation. It is also within the skill of the ordinary practitioner to select a monomer concentration and an initiator concentration to give polymerized products of the desired molecular weights, which depend upon the degree of polymerization of the acrylate moieties. Higher initiator concentrations will tend to produce products of lower average molecular weight. Other techniques will be apparent to a person of skill in the art.

Once the polymerization reaction has proceeded to the desired degree, the hydrogel can be dried. The drying, or dehydration of the polyalkyleneglycolyl polyacrylate matrix can be carried out by any suitable means. For example, the dehydration can take place using drying under a vacuum, such as at room temperature, or using lyophilization, i.e., drying at low temperatures wherein the water is in the solid state under a high vacuum. Once the matrix is dried, it can be used without further processing, or it can be comminuted to a powder, before proceeding to the next step.

Alternatively, microparticles can be formed directly using a suspension polymerization based on methods by Ascentiis, et al (*Journal of Controlled Release*, 33 (1995) 197-201). This synthesis utilizes the thermal initiator azobisisobutyronitrile (AIBN). Microparticles can be formed using the copolymerized polyethyleneglycolyl dimethacrylate/hydroxyethyl methacrylate systems.

In another embodiment, the hydrogel can be used directly in the next step of infusing the bioactive agent without further processing.

The bioactive agent such as the therapeutic protein is dissolved in a second aqueous medium prior to its infusion into the matrix, or alternatively it can be added in solid form to a hydrated suspension of the hydrogel. The bioactive agent can be dissolved in pure water, or buffered saline, or other aqueous medium that is supportive of the native configuration of the bioactive agent, or a cosolvent such as ethanol can be added if necessary to prepare the solution. The concentration of the bioactive agent can vary, depending on the identity and molecular properties of the agent and the dosage contemplated to be released by the inventive controlled release formulation. The aqueous medium can further contain stabilizers, surfactants and other ingredients as needed, with the understanding that any ingredient that will not be lost be evaporation in the subsequent drying step will be present in the controlled release formulation when it is emplaced within the body tissues of the patient.

The matrix is then soaked in the aqueous solution of the bioactive agent, for a suitable period such that the matrix absorbs the agent to form a hydrogel incorporating the bioactive agent. The matrix, particularly if it is at least partially dehydrated, imbibes the solution of the agent, for example the protein solution, preferably until equilibrium is reached and the hydrogel is saturated with the solution. The step of soaking the matrix can take place under any suitable conditions, for example, at room temperature overnight. Again, steps are preferably taken to avoid contamination, such as bacterial growth, through the use of suitable sterile techniques. The protein can be maintained in its native state during this process through the use of suitable buffers, anti-oxidants, stabilizers, and the like.

Once the hydrogel has reached saturation with the solution of the bioactive agent, the hydrogel is separated from any supernatant remaining, such as by decanting, filtering, centrifuging, or any other suitable technique. The hydrogel containing the bioactive agent, that is, the hydrated inclusion complex, is then dried to form the dehydrated inclusion complex of the bioactive agent within the polyalkyleneglycolyl polyacrylate matrix. Drying can take place by any suitable means as is well known in the art. Preferably, if the bioactive agent is a heat-sensitive material, such as a protein, high temperatures are avoided during drying. Drying can take place under a vacuum at room temperatures and below. Lyophilization can be used. Once drying is complete, the solid material can be ground or comminuted into a finely particulate form. Alternatively, if microparticles were formed in a previous step, the microparticles containing the aqueous solution of the bioactive agent can be dried by any suitable means, such as under a vacuum, to provide a microparticulate dehydrated inclusion complex of the invention.

The dehydrated inclusion complex can be stored under suitable conditions, for example at low temperatures under inert atmosphere, such as at −80° C. under nitrogen or argon, until use is contemplated. In one embodiment, the dehydrated inclusion complex in a suitable amount can be disposed within a syringe. A suitable amount can be the amount that would be administered to a single patient in a medically indicated dosage for treatment of a malcondition.

Mixing of the dehydrated inclusion complex with a solution of the biodegradable polymer can be accomplished as for any bioactive compound, for which procedures are provided in U.S. Pat. Nos. 6,565,874, 6,528,080, 6,461,631, 6,395,293, and references found therein, which are incorporated herein by reference. In certain embodiments, a solution of a PLG copolymer of weight average molecular weight in the range of about 15-50 kDa is made up at about 40-50 wt % in the organic solvent. N-methylpyrrolidone is an example of an organic solvent that readily dissolves the PLG copolymer and subsequently disperses within the patient's body tissues after emplacement of a depot of the controlled release formulation.

The dehydrated inclusion complex can be mixed with a solution of the biodegradable polymer in the organic solvent by any suitable means. For example, a solution of the biodegradable polymer can be disposed in a first container and the dehydrated inclusion complex disposed in a second container, and the contents of the two containers mixed when needed to provide the inventive controlled release formulation. The contents of the two containers can be mixed immediately prior to emplacement of the inventive controlled release formulation within the body tissues of a patient in need thereof. For example, the first container, the second container, or both, can comprise respective syringes. The biodegradable polymer solution can be disposed within a first syringe, and the dehydrated inclusion complex within a second syringe, and the two syringes coupled, for example using a Luer connector. The contents of the syringes can then be combined by transferring the solution from the first syringe into the second syringe, then reciprocally transferring the contents between the two syringes. The mixture can then be injected into a patient in need thereof in the form of a bolus, which forms a depot of the controlled release formulation in situ through diffusion of the organic solvent into the body fluids and the inflow of body fluids into the bolus.

The invention in another embodiment provides a kit for administration to a patient of the inventive controlled release formulation. The kit can comprise the first container, the second container, and instructional materials useful to a care provider. The first and the second container respectively contain the biodegradable polymer solution and the dehydrated inclusion complex, packaged in a manner to preserve sterility and to maximize stability of the components. For example, as mentioned above the two containers can each be a syringe with suitable fittings for containing and mixing the components to provide the controlled release formulation ready for injection into the patient's body tissues.

The invention provides a method of treatment of a malcondition comprising administering the inventive controlled release formulation comprising a bioactive agent that is medically indicated for treatment, prevention, or palliation of the malcondition to a patient in need thereof at a dosage level and for a duration effective to treat, prevent, or palliate the malcondition. The formulation of the invention is adapted for use of a macromolecular bioactive agent, as discussed above. It can also be used effectively with small molecule drugs such as peptides or organic molecules of molecular weight less than about 1,000 Da.

Concentrations, amounts, percentages, time periods, etc., of various components or use or effects of various components of this invention, including but not limited to the implants, indications of reduction in malcondition symptoms, and treatment time periods, are often presented in a range or baseline threshold format throughout this patent document. The description in range or baseline threshold format is merely for convenience and brevity and should not be construed as an inflexible limitation on the scope of the invention. Accordingly, the description of a range or baseline threshold should be considered to have specifically disclosed all the possible subranges as well as individual numerical values within that range or above that baseline threshold. For example, description of the molecular weight of the polyethyleneglycol moiety ranging between about 500

Da and about 10,000 Da should be considered to have specifically disclosed subranges, such as between about 750 Da and about 2,000 Da, between about 1000 Da and about 1500 Da, etc., as well as individual numbers within that range, such as about 700 Da, about 2500 Da, about 5000 Da, etc. This construction applies regardless of the breadth of the range or baseline threshold and in all contexts throughout this disclosure.

All publications, patents, and patent documents are incorporated by reference herein, as though individually incorporated by reference. The following Example is intended to illustrate the above invention and should not be construed as to narrow its scope. One skilled in the art will readily recognize that the specification and example suggest many other ways in which the present invention could be practiced. It should be understood that many variations and modifications may be made while remaining within the scope of the invention.

EXAMPLE

Formation of a Protein Inclusion Complex

A solution of between 5 and 50% PEG-methacrylate monomer in water with about 0.1 wt % 1-[4-(2-hydroxyethoxy)-phenyl]-2-hydroxy-2-methyl-1-propan-1-one (Irgacure 2959) is formed into a thin sheet, about 1 mm in thickness and irradiated with about 20 mW/cm$^2$ of 365 nm ultraviolet light for about 10 minutes. Then, the hydrogel is immersed in water for several days to aid in the removal of unreacted monomer. The gels are dried under vacuum at room temperature, ground to a powder at cryogenic temperatures. The resulting powder is then soaked in an aqueous solution of the protein, then filtered, rinsed, dried under vacuum at room temperature, then lyophilized overnight.

What is claimed is:

1. A formulation comprising a dehydrated inclusion complex dispersed in a solution;
    wherein the dehydrated inclusion complex comprises a protein stabilized within a hydrogel;
    wherein the hydrogel comprises a polymerized polyethyleneglycolyl dimethacrylate having a molecular weight from about 500 Daltons to about 10,000 Daltons, and
    wherein the solution consists of:
    (i) a poly(lactide-glycolide) copolymer, and
    (ii) N-methylpyrrolidone, dimethylacetamide, dimethylformamide, dimethylsulfoxide, a polyethyleneglycol, or a combination of two or more thereof.

2. The formulation of claim 1, wherein the polyalkyleneglycol diacrylate has a molecular weight of about 750 Daltons to about 2,000 Daltons.

3. The formulation of claim 1, wherein the protein is a monoclonal antibody.

4. The formulation of claim 1, wherein the protein is insulin, human growth hormone, cetuximab, or bevacizumab.

5. The formulation of claim 1, wherein the hydrogel particles are present in a concentration of about 5 wt % to about 50 wt %.

6. A formulation comprising:
    (i) a dehydrated inclusion complex comprising a protein stabilized within a hydrogel; wherein the hydrogel comprises a polyalkyleneglycol diacrylate;
    (ii) a biodegradable polymer consisting of a poly(lactide-glycolide) copolymer; and
    (iii) N-methylpyrrolidone, dimethylacetamide, dimethylformamide, dimethylsulfoxide, a polyethyleneglycol, or a combination of two or more thereof.

7. The formulation of claim 6, wherein the polyalkyleneglycol diacrylate has a molecular weight of about 500 Daltons to about 10,000 Daltons.

8. The formulation of claim 6, wherein the polyalkyleneglycol diacrylate is a polyalkyleneglycolyl dimethacrylate.

9. The formulation of claim 6, wherein the polyalkyleneglycolyl diacrylate is a polyethyleneglycolyl dimethacrylate.

10. The formulation of claim 6, wherein the protein is insulin, human growth hormone, cetuximab, or bevacizumab.

11. The formulation of claim 6, wherein the protein is a monoclonal antibody.

* * * * *